US008388998B2

(12) United States Patent
Friesen et al.

(10) Patent No.: US 8,388,998 B2
(45) Date of Patent: Mar. 5, 2013

(54) METHODS AND COMPOSITIONS FOR THE PREVENTION AND TREATMENT OF INFLAMMATORY DISEASES

(75) Inventors: Kim Gene Friesen, Carthage, IN (US); Ryan Michael Yamka, Topeka, KS (US)

(73) Assignee: Hill's Pet Nutrition, Inc., Topeka, KS (US)

(*) Notice: Subject to any disclaimer, the term of this patent is extended or adjusted under 35 U.S.C. 154(b) by 436 days.

(21) Appl. No.: 11/994,344

(22) PCT Filed: Jun. 29, 2006

(86) PCT No.: PCT/US2006/025395
§ 371 (c)(1), (2), (4) Date: Jul. 17, 2008

(87) PCT Pub. No.: WO2007/002837
PCT Pub. Date: Jan. 4, 2007

(65) Prior Publication Data
US 2009/0202657 A1   Aug. 13, 2009

Related U.S. Application Data

(60) Provisional application No. 60/695,151, filed on Jun. 29, 2005.

(51) Int. Cl.
*A23K 1/17* (2006.01)
(52) U.S. Cl. .................................................... 424/442
(58) Field of Classification Search .................. None
See application file for complete search history.

(56) References Cited

U.S. PATENT DOCUMENTS

| | | | |
|---|---|---|---|
| 5,339,771 A | 8/1994 | Axelrod | |
| 5,419,283 A | 5/1995 | Leo | |
| 5,480,872 A * | 1/1996 | Cope et al. | 514/3.8 |
| 5,766,621 A | 6/1998 | Trimbo | |
| 5,776,913 A * | 7/1998 | Ogilvie et al. | 514/57 |
| 5,817,695 A * | 10/1998 | Pellico | 514/558 |
| 6,008,252 A * | 12/1999 | Beale | 514/563 |
| 6,544,547 B2 | 4/2003 | Hageman | |
| 6,596,303 B1 | 7/2003 | Bui et al. | |
| 2003/0069202 A1 | 4/2003 | Kern et al. | |
| 2003/0194478 A1 | 10/2003 | Davenport et al. | |
| 2004/0001817 A1 | 1/2004 | Giampapa | |
| 2004/0234579 A1* | 11/2004 | Finke | 424/442 |
| 2004/0253296 A1 | 12/2004 | Martin et al. | |
| 2006/0280840 A1 | 12/2006 | Robertson | |

FOREIGN PATENT DOCUMENTS

| | | |
|---|---|---|
| AU | 568014 | 12/1987 |
| JP | 3-272652 A | 12/1991 |
| JP | 7-213233 A | 8/1995 |
| JP | 8-38063 A | 2/1996 |
| WO | WO 94/22453 | 10/1994 |
| WO | WO 99/03365 | 1/1999 |
| WO | WO 02/089842 | 11/2002 |
| WO | WO 2004/112776 | 12/2004 |

OTHER PUBLICATIONS

Kris-Etherton et al "Fish Consumption, Fish Oil, Omega-3 Fatty Acids, and Cardiovascular Disease", Circulation, 2002; 106; p. 2747-2757.*
"Corn Oil" Wikipedia pp. 1-3 (http://en.wikipedia.org/wiki/Corn_oil).*
Wikipedia "Horse" (pp. 1-3; retrieved online on Jan. 24, 2012; http://en.wikipedia.org/wiki/Horse).*
"Corn Oil" Wikipedia pp. 1-3 (http://en.wikipedia.org/wiki/Corn_oil); date retrieved online Mar. 22, 2011.*
International Search Report (Mar. 5, 20007).
Supplementary European Search Report (Jul. 21, 2008).
Official Publication Association of American Feed Control Officials Incorporated , pp. 129-137 (2004).
Allan et al., "Animal Model of Human Disease," Pathology, 81(3): 699-702, Dec. 1975.
"Post Marketing Surveillance Open Study: The Use of Lyproflex Equine in the Management of Lameness," 2002, pp. 1-5.
ARTHRIMAXX™ from Publication KVV, Section: Nutritionals, pp. 1-7 (http://e-ditionsfry.com/Olive/ODE/KVV/PrintComponentView.htm; retrieved online on Dec. 22, 2011.
Bierer et al., 2002, "Waltham International Symposium: Pet Nutrition Comping of Age Improvement of Arthritic Signs in Dogs Fed Green-Lipped Mussel (*Perna cananliculus*)," J. Nutrition 132:1634S-1636S.
Borregaard et al., 1987, "Prevention of Tissue Damage. Inhibition of Myeloperoxidase Mediated Inactivation of $\alpha_1$-Proteinase Inhibitor by N-Acetyl Cysteine, Glutathione, and Methionine," Agents and Actions 22(3/4):255-260.
Hielm-Bjorkman et al., 2007, Evaluating Complementary Therapies for Canine Osteoarthritis Part I: Green-Lipped Mussel (*Perna canaliculus*), Advanced Access Publication Oct. 29, 2007, eCAM 6(3):365-373.
Royal Canin Veterinary Diet™ Product Sheet for Mobility Support JS, pp. 1-2 (http://walthamusa.com/Learning%Center/JS21.html; retrived online on Dec. 22, 2011).
Terano, 1987, "Eicosapentaenoic Acid," Japanese J. of Inflammation 7(1):63-71.
Nakamoto, 2002, "A New Perspective on Nutrition from the Mouth to the Whole Body: The Role of Manganese As a Nutrient," The Quintessence 21(2):297-298.

* cited by examiner

*Primary Examiner* — Bethany Barham
(74) *Attorney, Agent, or Firm* — Shannon McGarrah

(57) ABSTRACT

The invention provides compositions for preventing or treating inflammatory disease comprising one or more omega-3 fatty acids, one or more sulfur containing amino acids, and manganese and methods for preventing and treating inflammatory disease comprising administering such compositions to an animal susceptible to or suffering from inflammatory disease. In a preferred embodiment, the composition is admixed with one or more food ingredients to produce a food composition useful for preventing or treating inflammatory disease.

7 Claims, No Drawings

METHODS AND COMPOSITIONS FOR THE PREVENTION AND TREATMENT OF INFLAMMATORY DISEASES

CROSS-REFERENCE TO RELATED APPLICATIONS

This application is a national stage entry under 35 U.S.C. §371 of International Application No. PCT/US06/025395, filed Jun. 29, 2006, which claims priority to U.S. Provisional Application Ser. No. 60/695,151 filed Jun. 29, 2005, the disclosures of which are incorporated herein by reference.

BACKGROUND OF THE INVENTION

1. Field of the Invention

This invention relates generally to compositions and methods for combating inflammatory disease and particularly to the use of food compositions for preventing and treating inflammatory disease.

2. Description of the Prior Art

Polyunsaturated fatty acids (PUFAs) are compounds reported to be beneficial for treatment of inflammation-related disorders such as arthritis. Omega-3 fatty acids are one type of PUFA that contain more than one double bond. They are called omega-3 fatty acids because the first double bond counting from the methyl end of the fatty acid is located at the third carbon atom.

Omega-3 fatty acids are considered essential fatty acids because they are essential to health but cannot be manufactured by the body. Therefore, omega-3 fatty acids must be obtained from food or food supplements. Omega-3 fatty acids are in fish and certain plant oils. There are three major types of omega-3 fatty acids in foods, i.e., alpha-linolenic acid (ALA; 18:3n-3), eicosapentaenoic acid (EPA; 20:5n-3), and docosahexaenoic acid (DHA; 22:6n-3). ALA is considered an essential fatty acid because it is required for health but cannot be synthesized by mammals. Mammals can, however, synthesize other omega-3 fatty acids from ALA, including EPA and DHA.

Omega-3 fatty acids are known to have a wide range of nutritional and health benefits such as reducing inflammation and treating inflammation-related disorders. Omega-3 fatty acids are thought to be important in arthritis, brain function, visual acuity, and normal growth and development. Omega-3 fatty acids have also been reported to act as anti-inflammatory compounds. They are believed to competitively inhibit the conversion of arachidonic acid to pro-inflammatory eicosanoids. Omega-3 fatty acids are also precursors to the synthesis of prostaglandins that regulate inflammation in mammals.

Rheumatism and arthritis are general terms for acute and chronic conditions characterized by inflammation and pain. Rheumatism is a general category of conditions characterized by inflammation and pain in muscles and joints, including arthritis. Arthritis is characterized by inflammation of joints that causes swelling and pain. Types of arthritis include osteoarthritis, rheumatoid arthritis, ankylosing spondylitis (AS), and systemic lupus erythematosus (SLE). Rheumatic conditions include infectious arthritis, rheumatoid arthritis, arthritis due to rheumatic fever, arthritis due to trauma or degenerative joint disease, myositis, neurogenic arthropathy, bursitis, fibromyositis and hydroarthrosis. The cause of such diseases in not always fully understood but may be the result of other degenerative diseases, trauma, or auto-immune diseases such as SLE. Inflammation also occurs as a defensive response to host invasion by foreign agents and mechanical trauma that results in an immune response, e.g., microbial agents such as bacterial and viruses, toxins, and neoplasia.

What these diseases and conditions, both examples of inflammatory diseases, share in common is inflammation and the resulting pain. Prior methods for preventing and treating inflammatory diseases have generally focused on pain-killing and anti-inflammatory drugs. Typical methods have focused on oral medications such as steroidal cortisone derivatives and numerous non-steroidal anti-inflammatory drugs (NSAIDs). Unfortunately, these drugs almost always exhibit undesirable side effects. Other efforts have focused on joint implants such as the knee or hip implants. These methods are lengthy and complicated surgical procedures that force the patient to undergo costly invasive surgery and a significant recovery period requiring a rigorous and costly regimen of physical therapy. There is, therefore, a need for new methods for preventing and treating inflammatory diseases that avoids the undesirable side effects and costly surgical procedures characteristic of previous methods for preventing and treating inflammatory diseases.

SUMMARY OF THE INVENTION

It is, therefore, an object of the present invention to provide compositions and methods for preventing and treating inflammatory disease.

It is another object of the invention to provide food compositions for preventing and treating inflammatory disease.

It is another object of the invention to provide articles of manufacture in the form of kits that contain combinations of compositions and devices useful for preventing and treating inflammatory disease.

It is a further object of the invention to decrease the morbidity and mortality caused by inflammatory disease.

These and other objects are achieved using novel compositions and methods for preventing or treating inflammatory disease. The compositions comprise one or more omega-3 fatty acids, one or more sulfur containing amino acids, and manganese in amounts sufficient for preventing or treating inflammatory diseases, typically at least 30 mg/kg/day omega-3 fatty acids, at least 1 mg/kg/day sulfur containing amino acids, and at least 0.005 mg/kg/day manganese. Food compositions comprising one or more food ingredients and the compositions are preferred. The methods comprise administering such compositions to patients susceptible to or suffering from inflammatory disease. Kits comprising the composition components (omega-3 fatty acids, sulfur containing amino acids, and manganese) and one or more optional feed ingredients and anti-inflammatory drugs are provided.

Other and further objects, features, and advantages of the present invention will be readily apparent to those skilled in the art.

DETAILED DESCRIPTION OF THE INVENTION

Definitions

The term "patient" means a human or other animal likely to develop or suffering from inflammatory disease, including avian, bovine, canine, equine, feline, hicrine, murine, ovine, and porcine animals. Preferably, the patient is a canine or feline.

The term "anti-inflammatory drug" means any compound, composition, or drug useful for preventing or treating inflammatory disease.

The term "in conjunction" means that one or more of the compositions and compounds (e.g., anti-inflammatory drugs or composition components) of the present invention are administered to a patient (1) together in a food composition or (2) separately at the same or different frequency using the same or different administration routes at about the same time or periodically. "Periodically" means that the compositions, food compositions, and compounds are administered on a dosage schedule acceptable for a specific composition, food composition, and compound and that the food compositions are administered or fed to a patient routinely as appropriate for the particular patient. "About the same time" generally means that the compositions, composition components, anti-inflammatory drugs, and food compositions are administered at the same time or within about 72 hours of each other. In conjunction specifically includes administration schemes wherein anti-inflammatory drugs are administered for a prescribed period and the compositions are administered indefinitely.

The term "single package" means that the components of a kit are physically associated in or with one or more containers and considered a unit for manufacture, distribution, sale, or use. Containers include, but are not limited to, bags, boxes, bottles, shrink wrap packages, stapled or otherwise affixed components, or combinations thereof.

The term "virtual package" means that the components of a kit are associated by directions on one or more physical or virtual kit components instructing the user how to obtain the other components, e.g., in a bag containing one component and directions instructing the user to go to a website, contact a recorded message, view a visual message, or contact a caregiver or instructor to obtain instructions on how to use the kit.

This invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise, e.g., reference to "a method" or "a food composition" includes a plurality of such methods or compositions. Similarly, the words "comprise", "comprises", and "comprising" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents, patent applications, and publications mentioned herein are incorporated herein by reference to the extent allowed by law for the purpose of describing and disclosing the compounds, processes, techniques, procedures, technology, articles, and other compositions and methods disclosed therein that might be used with the present invention. However, nothing herein is to be construed as an admission that the invention is not entitled to antedate such disclosure by virtue of prior invention.

The Invention

In one aspect, the present invention provides a composition for preventing and treating inflammatory disease. The composition comprises one or more omega-3 fatty acids, one or more sulfur containing amino acids, and manganese in amounts sufficient for preventing or treating inflammatory disease. The invention is based upon the novel discovery that the inflammatory response can be altered by administering the composition to a patient and that altering inflammatory response with the composition can prevent or treat inflammatory disease. Without being bound by theory, it is believed that composition is effective in preventing and treating inflammatory disease because it reduces the amount of proinflammatory mediators in a patient.

Typically, the composition comprises one or more omega-3 fatty acids, one or more sulfur containing amino acids, and manganese in amounts sufficient to administer to a patient at least 30 mg/kg/day omega-3 fatty acids, at least 1 mg/kg/day sulfur containing amino acids, and at least 0.005 mg/kg/day manganese. Preferably, the composition comprises from about 30 mg/kg/day to about 3000 mg/kg/day omega-3 fatty acids, from about 1 mg/kg/day to about 200 mg/kg/day sulfur containing amino acids, and from about 0.005 mg/kg/day to about 10 mg/kg/day manganese. Most preferably, the composition comprises from about 100 mg/kg/day to about 1500 mg/kg/day omega-3 fatty acids, from about 10 mg/kg/day to about 100 mg/kg/day sulfur containing amino acids, and from about 0.05 mg/kg/day to about 5 mg/kg/day manganese. The compositions contain omega-3 fatty acids, sulfur containing amino acids, and manganese in amounts that are not deleterious to a patient's health, e.g., amounts that do not cause undesirable toxic effects in the patient.

Any omega-3 fatty acid can be used in the present invention. Preferably, the omega-3 fatty acids are ALA, DHA, and EPA, most preferably EPA. Omega-3 fatty acids can be obtained from any common source known to skilled artisans. Omega-3 fatty acids are found in foods such as fish (e.g., salmon and tuna), fish oil, flaxseed, canola oil, and walnuts. Omega-3 fatty acids can be obtained in purified form from several commercial manufacturers.

Any sulfur containing amino acid can be used in the present invention. Preferably, the sulfur containing amino acids are methionine, cystine, and taurine. Most preferably, the sulfur containing amino acid is methionine. Methionine (2-amino-4-methylthiobutyric acid) acts as an antioxidant and plays a role in the breakdown of fats and the removal of heavy metals from the body. Methionine is found in good quantities in meat, fish, beans, eggs, garlic, lentils, onions, yogurt and seeds. Sulfur containing amino acids are common amino acids available to skilled artisans.

Manganese is an essential trace mineral available to skilled artisans. Manganese acts as a catalyst and cofactor in many enzymatic processes involved in the synthesis of fatty acids and cholesterol, mucopolysaccharide synthesis (in bones, collagen, and connective tissue), and in the synthesis of glycoproteins. Manganese is found in tea, whole grains, nuts, and avocados and somewhat in fruits and vegetables.

The composition, methods, and kits of the present invention are useful to prevent or treat any inflammatory disease, including rheumatism and arthritis. The invention is particularly useful for the prevention or treatment of arthritis.

In another aspect, the present invention provides a food composition for preventing and treating inflammatory disease. The food composition comprises one or more food ingredients admixed with one or more omega-3 fatty acids, one or more sulfur containing amino acids, and manganese in amounts sufficient for preventing or treating inflammatory disease. Generally, the food composition comprises one or more food ingredients and the omega-3 fatty acids, sulfur containing amino acids, and manganese in amounts sufficient to administer to a patient at least 30 mg/kg/day omega-3 fatty acids, at least 1 mg/kg/day sulfur containing amino acids, and at least 0.005 mg/kg/day manganese. Preferably, the composition comprises one or more food ingredients and from about 30 mg/kg/day to about 3000 mg/kg/day omega-3 fatty acids, from about 1 mg/kg/day to about 200 mg/kg/day sulfur containing amino acids, and from about 0.005 mg/kg/day to about 10 mg/kg/day manganese. Most preferably, the composition comprises one or more food ingredients and from about 100 mg/kg/day to about 1500 mg/kg/day omega-3 fatty acids, from about 10 mg/kg/day to about 100 mg/kg/day sulfur containing amino acids, and from about 0.05 mg/kg/day to about 5 mg/kg/day manganese.

The food ingredients useful in the present invention include any food ingredient suitable for consumption by a patient. Typical food ingredients include but are not limited to fats, carbohydrates, proteins, fibers, and nutrients such as vitamins, minerals, and trace elements. Skilled artisans can select the amount and type of food ingredients for a typical food based upon the dietary requirements of the patient, e.g., the patient's species, age, size, weight, health, and function.

The food ingredient part of the food composition can comprise 100% of any particular food ingredient or can comprise a mixture of food ingredients in various proportions. In preferred embodiments, the food composition comprises a combination of food ingredients in amounts from about 0% to about 50% fat, from about 0% to about 75% carbohydrate, from about 0% to about 95% protein, from about 0% to about 40% dietary fiber, and from about 0% to about 15% of one or more nutrients.

The fat and carbohydrate food ingredient is obtained from a variety of sources such as animal fat, fish oil, vegetable oil, meat, meat by-products, grains, other animal or plant sources, and mixtures thereof. Grains include wheat, corn, barley, grain sorghum, and rice.

The protein food ingredient is obtained from a variety sources such as plants, animals, or both. Animal protein includes meat, meat by-products, dairy, and eggs. Meats include the flesh from poultry, fish, and animals such as cattle, swine, sheep, goats, and the like. Meat by-products include lungs, kidneys, brain, livers, stomachs, and intestines. The protein food ingredient may also be free amino acids and/or peptides. Preferably, the protein food ingredient comprises meat, a meat by-product, dairy products, or eggs.

The fiber food ingredient is obtained from a variety of sources such as vegetable fiber sources, e.g., cellulose, beet pulp, peanut hulls, and soy fiber.

The nutrients are obtained from a variety of sources known to skilled artisans, e.g., vitamin and mineral supplements and food ingredients. Vitamins and minerals can be included in amounts required to avoid deficiency and maintain health. These amounts are readily available in the art. The National Research Council (NRC) provides recommended amounts of such nutrients for farm animals. See, e.g., Nutrient Requirements of Swine (10th Rev. Ed., Nat'l Academy Press, Wash. D.C., 1998), Nutrient Requirements of Poultry (9th Rev. Ed., Nat'l Academy Press, Wash. D.C., 1994), Nutrient Requirements of Horses (5th Rev. Ed., Nat'l Academy Press, Wash. D.C., 1989). The American Feed Control Officials (AAFCO) provides recommended amounts of such nutrients for dogs and cats. See American Feed Control Officials, Inc., Official publication, pp. 129-137 (2004). Vitamins generally useful as food additives include vitamin A, vitamin B1, vitamin B2, vitamin B6, vitamin B12, vitamin D, biotin, vitamin K, folic acid, inositol, niacin, and pantothenic acid. Minerals and trace elements useful as food additives include calcium, phosphorus, sodium, potassium, magnesium, copper, zinc, chloride, iron, selenium, iodine, and iron.

The compositions and food compositions may contain additional ingredients such as vitamins, minerals, fillers, palatability enhancers, binding agents, flavors, stabilizers, emulsifiers, sweeteners, colorants, buffers, salts, coatings, and the like known to skilled artisans. Stabilizers include substances that tend to increase the shelf life of the composition such as preservatives, synergists and sequestrants, packaging gases, stabilizers, emulsifiers, thickeners, gelling agents, and humectants. Examples of emulsifiers and/or thickening agents include gelatin, cellulose ethers, starch, starch esters, starch ethers, and modified starches. Specific amounts for each composition component, food ingredient, and other ingredients will depend on a variety of factors such as the particular components and ingredients included in the composition; the species of patient; the patient's age, body weight, general health, sex, and diet; the patient's consumption rate; the type of inflammatory disease being treated; and the like. Therefore, the component and ingredient amounts may vary widely and may deviate from the preferred proportions described herein.

The food compositions may be prepared in a canned or wet form using conventional food preparation processes known to skilled artisans. Typically, ground animal proteinaceous tissues are mixed with the other ingredients such as fish oils, cereal grains, balancing ingredients, special purpose additives (e.g., vitamin and mineral mixtures, inorganic salts, cellulose and beet pulp, bulking agents, and the like) and water in amounts sufficient for processing. These ingredients are mixed in a vessel suitable for heating while blending the components. Heating of the mixture is effected using any suitable manner, e.g., direct steam injection or using a vessel fitted with a heat exchanger. Following the addition of the last ingredient, the mixture is heated to a temperature of from about 50° F. to about 212° F. Temperatures outside this range are acceptable but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. Sterilization is usually accomplished by heating to temperatures of greater than about 230° F. for an appropriate time depending on the temperature used, the composition, and similar factors. The compositions of the present invention can be added to the food compositions before, during, or after preparation.

The food compositions may be prepared in a dry form using conventional processes known to skilled artisans. Typically, dry ingredients such as animal protein, plant protein, grains, and the like are ground and mixed together. Moist or liquid ingredients, including fats, oils, animal protein, water, and the like are then added to and mixed with the dry mix. The mixture is then processed into dry food pieces.

The food compositions can be in any form useful for feeding the composition to a patient, e.g., kibbles, treats, and toys for animal food. Kibbles are generally formed using an extrusion process in which the mixture of dry and wet ingredients is subjected to mechanical work at a high pressure and temperature and forced through small openings and cut off into kibble by a rotating knife. The wet kibble is then dried and optionally coated with one or more topical coatings such as flavors, fats, oils, powders, and the like. Kibble also can be made from the dough using a baking process, rather than extrusion, wherein the dough is placed into a mold before dry-heat processing. Treats include compositions that are given to an animal to entice the animal to eat during a non-meal time, e.g., dog bones or biscuits for canines. Treats may be nutritional wherein the composition comprises one or more nutrients or and may have a food-like composition. Non-nutritional treats encompass any other treats that are non-toxic. The composition or components are coated onto the treat, incorporated into the treat, or both. Treats of the present invention can be prepared by an extrusion or baking process similar to those used for dry food. Other processes also may be used to either coat the composition on the exterior of existing treat forms or inject the composition into an existing treat form. Toys include chewable toys such as artificial bones and food compositions shaped to resemble natural foods that are appealing to the animal. The food composition of the present invention can comprise the toy or can form a coating on the surface of the toy or on the surface of a component of the toy. The composition can be incorporated partially or fully throughout the toy or both. In one embodiment, the composition is orally accessible by the intended user. There are a wide range of suitable toys known to skilled artisans, e.g., as shown in U.S. Pat. Nos. 5,339,771 and 5,419,283. The present invention encompasses partially consumable toys, e.g., toys comprising plastic components, and fully consumable toys, e.g., various artificial bones and similar foods. Further, the invention encompasses toys for both human and non-human use, particularly toys for companion, farm, and zoo animal use, and more particularly for feline and canine use.

In another aspect, the present invention provides compositions and food compositions of the present invention further comprising one or more anti-inflammatory drugs. Anti-inflammatory drugs useful in the invention are any anti-inflammatory drugs known to skilled artisans to be useful for combating inflammatory disease. Useful drugs include Ketoprofen D C, Meloxican D C, Carprofen D C, Etodolac D, Deracoxib D, Tepoxalin D, Tolfenamic acid D C, Ketorolac D C, Piroxicam D, Acetaminophen D, Aspirin D. Holistic anti-inflammatory drugs and compositions are also included in the present invention. Preferred holistic anti-inflammatory drugs include glucosamine, chondroitin sulfate, green lippedussel, methylsulfonyl methane, and trace minerals such as zinc, manganese, and copper. Anti-inflammatory drugs include typical small molecule pharmaceuticals, small proteins, macromolecular proteins and molecules, and antibodies and further include vaccines designed to prevent inflammatory disease. Antibodies include polyclonal and monoclonal antibodies and immunoglobulin fragments such as Fv, Fab, Fab', F(ab')2, or other antigen-binding antibody subsequences that interact with an antigen and perform the same biological function as a native antibody. The anti-inflammatory drugs are administered to the patient using any method appropriate for the anti-inflammatory drug and in amounts known to skilled artisans to be sufficient to treat or prevent inflammatory disease.

In a further aspect, the present invention provides methods for preventing and treating inflammatory disease. The methods comprise administering to a patient an inflammatory disease preventing or treating amount of a composition comprising one or more omega-3 fatty acids, one or more sulfur containing amino acids, and manganese. The methods also comprise administering in conjunction to a patient an inflammatory disease preventing or treating amount of a composition comprising one or more omega-3 fatty acids, one or more sulfur containing amino acids, and manganese and an anti-inflammatory drug. The methods further comprise administering the composition in conjunction with a food composition comprising one or more food ingredients. In a preferred embodiment, the composition and the food ingredients are administered in a food composition comprising an admixture of the composition and the food ingredients. In preferred embodiments, the patient is a feline or a canine. The preferred omega-3 fatty acids are ALA, DHA, and EPA, most preferably EPA.

The methods are accomplished by administering the compositions to the patient in various forms. For example, one or more composition components and food ingredients are in separate containers and admixed just prior to administration. In one embodiment, one or more omega-3 fatty acids, one or more sulfur containing amino acids, and manganese are admixed in one container and the resulting composition mixed with food ingredients just prior to administration, e.g., by stirring the composition into or sprinkling the composition onto the food ingredients. In another, one or more of the composition components are admixed with the food ingredients during manufacture and the remaining composition components admixed with such food ingredients just prior to administration. In a further, the composition is a component of a pour-on formulation, preferably containing vitamins and minerals, that is applied to food ingredients prior to administration. In another, the composition is admixed with one or more food ingredients and such admixture is mixed with other food ingredients before administration. In a further, the composition is coated onto the food ingredients during the manufacturing process or after the food composition is manufactured. In another, the composition is administered orally and the food composition is fed to the patient.

The compositions are administered to the patient using any suitable method, preferably by feeding the compositions to the patient. The composition is administered orally using any suitable form for oral administration, e.g., tablets, pills, suspensions, solutions (possibly admixed with drinking water), emulsions, capsules, powders, syrups, and palatable feed compositions (a confectionery for a human or a treat or flavored treat for an animal). In a preferred embodiment, the composition components and the food ingredients are admixed during manufacture process used to prepare the food composition suitable for administration in the form of a food for consumption by the patient.

A further method comprises administering the composition or food composition of the present invention in conjunction with one or more anti-inflammatory drugs. Typically, health care professionals, e.g., doctors and veterinarians, diagnose inflammatory disease in a patient and prescribe an anti-inflammatory drug (any drug useful to prevent or treat inflammatory disease in a patient) to treat the disease. The patient is administered the anti-inflammatory drug until the symptoms cease and the disease is considered cured. Generally, the anti-inflammatory drug is not administered after the disease is considered cured. Administration of the anti-inflammatory drug is resumed only if the patient has a reoccurrence of the inflammatory disease. In the present invention, the compositions and anti-inflammatory drugs are administered in conjunction to the patient during treatment. After administration of the anti-inflammatory drug ceases, the compositions are administered to the patient to prevent reoccurrence of the disease. In another embodiment, the compositions are administered to the patient only after use of the anti-inflammatory drug is discontinued to prevent disease reoccurrence.

In another aspect, the present invention provides methods for manufacturing a food composition suitable for preventing and treating inflammatory disease. The methods comprise admixing one or more food ingredients suitable for consumption by a patient with one or more omega-3 fatty acids, one or more sulfur containing amino acids, and manganese in amounts sufficient for preventing or treating inflammatory disease. In one embodiment, the food composition comprises one or more food ingredients and the omega 3 fatty acids, sulfur containing amino acids, and manganese in amounts sufficient to administer to a patient at least 30 mg/kg/day omega-3 fatty acids, at least 1 mg/kg/day sulfur containing amino acids, and at least 0.005 mg/kg/day manganese.

In a further aspect, the present invention provides a kit suitable for administering an inflammatory disease preventing or treating composition to a patient comprising in separate containers in a single package or in a virtual package, as appropriate for the kit component, two or more of (1) one or more omega-3 fatty acids, (2) one or more sulfur containing amino acids, (3) manganese, (4) one or more food ingredients, (5) one or more anti-inflammatory drugs, (6) a means for communicating information about or instructions for admixing one or more food ingredients suitable for consumption by a patient with one or more omega-3 fatty acids, one or more sulfur containing amino acids, and manganese in amounts sufficient for preventing or treating inflammatory disease to produce a food composition suitable for preventing and treating inflammatory disease, (7) a means for communicating information about or instructions for using a food composition comprising one or more food ingredients admixed with one or more omega-3 fatty acids, one or more sulfur containing amino acids, and manganese in amounts sufficient for preventing or treating inflammatory disease, and (8) a means for communicating information about or instructions for administering in conjunction a food composition comprising one or more food ingredients admixed with one or more omega-3 fatty acids, one or more sulfur containing amino acids, and manganese in amounts sufficient for preventing or treating inflammatory disease and an anti-inflammatory drug for preventing or treating inflammatory disease.

The kits of the present invention contain the kit components in any of various combinations and/or mixtures. For example, one kit comprises one or more omega-3 fatty acids, one or more sulfur containing amino acids, and manganese in separate containers. The kit components are mixed with one or more food ingredients to produce a food composition containing the ingredients. Another kit comprises one or more omega-3 fatty acids, one or more sulfur containing amino acids, manganese and one or more food ingredients in separate containers. The kit components are admixed to produce a food composition containing the ingredients, typically just prior to administering the resulting food composition to a patient. A similar kit contains a mixture of two of the components on a single container and the other components in a separate container, e.g., sulfur containing amino acids and manganese in a single container, the fatty acids in a separate container, and the food ingredients in a separate container (or the fatty acids and food ingredients together in a separate container). A further kit comprises a food composition comprising one or more food ingredients admixed with one or more omega-3 fatty acids, one or more sulfur containing amino acids, and manganese in amounts sufficient for preventing or treating inflammatory disease in one container and an anti-inflammatory drug in a separate container. Another kit comprises a food composition comprising one or more food ingredients admixed with one or more omega-3 fatty acids, one or more sulfur containing amino acids, and manganese in amounts sufficient for preventing or treating inflammatory disease in one container and a means for communicating information about or instructions for using a food composition comprising one or more food ingredients admixed with one or more omega-3 fatty acids, one or more sulfur containing amino acids, and manganese in amounts sufficient for preventing or treating inflammatory disease in a separate or virtual container. Numerous such combinations can be constructed by the skilled artisan.

The kit components are typically in a separate package, in or on the package with one of the other kit components, or in a virtual package, as appropriate for the type of kit component. When the kit comprises a virtual package, the kit is limited to the instructions in a virtual environment in combination with one or more of the other physical kit components.

The kits contain the omega-3 fatty acids, sulfur containing amino acids, and manganese in amounts sufficient to supply to a patient at least 30 mg/kg/day omega-3 fatty acids, at least 1 mg/kg/day sulfur containing amino acids, and at least 0.005 mg/kg/day manganese.

In another aspect, the present invention provides a means for communicating information about or instructions for (1) using a food composition comprising one or more food ingredients admixed with one or more omega-3 fatty acids, one or more sulfur containing amino acids, and manganese in amounts sufficient for preventing or treating inflammatory disease, (2) administering in conjunction a food composition comprising one or more food ingredients admixed with one or more omega-3 fatty acids, one or more sulfur containing amino acids, and manganese in amounts sufficient for preventing or treating inflammatory disease and an anti-inflammatory drug for preventing or treating inflammatory disease, (3) admixing one or more food ingredients suitable for consumption by a patient with one or more omega-3 fatty acids, one or more sulfur containing amino acids, and manganese in amounts sufficient for preventing or treating inflammatory disease to produce a food composition suitable for preventing and treating inflammatory disease, and (4) using a kit of the present invention for preventing and treating inflammatory disease. The communicating means comprises a document, digital storage media, optical storage media, audio presentation, or visual display containing the information or instructions. Preferably, the communication is a displayed website or a brochure, product label, package insert, advertisement, or visual display containing such information or instructions. Useful information includes, but is not limited to, one or more of (1) methods and techniques for manufacturing and/or administering the food compositions of the invention, with or without anti-inflammatory drugs, (2) details about the side effects, if any, caused by using the present invention in combination with other drugs, and (3) contact information for patients to use if they have a question about the invention and its use. Useful instructions include, but are not limited to, dosages, administration amounts, administration frequency, and administration routes. The communication means is useful for instructing a patient on the benefits of using the present invention and communicating the approved methods for administering the invention to a patient.

In another aspect, the present invention provides methods for inhibiting or preventing the release of proinflammatory mediators. The methods comprise administering to a patient a proinflammatory mediator release inhibiting or preventing amount of a composition comprising one or more omega-3 fatty acids, one or more sulfur containing amino acids, and manganese to a patient. Proinflammatory mediators include, but are not limited to, proinflammatory cytokines, chemokines, and proteases.

All percentages expressed herein are on a weight by dry matter basis unless specifically stated otherwise. All weights and concentrations for the compositions of the present invention are based on dry weight of a composition after all components and ingredients are admixed. The dosages expressed herein are in milligrams per kilogram of body weight per day (mg/kg/day) unless expressed otherwise.

The compositions, methods, and kits are useful for decreasing the morbidity and mortality for patients susceptible to or suffering from inflammatory disease.

EXAMPLES

This invention can be further illustrated by the following examples of preferred embodiments thereof, although it will be understood that these examples are included merely for purposes of illustration and are not intended to limit the scope of the invention unless otherwise specifically indicated.

Example 1

Canine Study

Study Design: This study utilized 10 healthy geriatric beagle dogs (10 years old or over) per group (40 dogs total). The dogs were determined to be healthy by physical exam and blood chemistry screen. Dogs with confirmed renal failure, cancer, arthritis, hypothyroidism or other diseases were excluded. The dogs were cared for in accordance with Institutional Animal Care and Use Committee protocols. The study design utilized a 30 day pre-feeding period followed by a 6 month test feeding period for a total of 7 months.

During the 30 day pre-feeding period, all dogs were fed a control formula food. During the last week of the pre-feeding period, blood and urine samples were taken from each animal. Dual-energy x-ray absorptiometry (DXA) scans and Tekscan pressure map analysis were also performed. The dogs were then blocked by age, gender and body fat percentage and assigned to 4 different treatment groups. Each group of dogs was randomly assigned to receive either the new Geriatric food or one of three competitor products.

During the 7 month test period, blood samples were drawn at 1 month, 3 months and 6 months for analysis of biomarkers. Dogs were scanned by DXA at 3 months and 6 months to document changes in body composition and bone density. In addition, at 1 month, 3 months and 6 months the dogs were walked across the Tekscan pressure map to determine effects of the foods on joint health. Throughout the duration of the study, body weights were recorded weekly and food intake recorded daily. Additionally, dogs were offered enrichment toys, received routine grooming and had daily opportunities for socialization with other dogs and people.

Data was taken according to the Study Schedule shown below. The foods used in the study are shown in the Study Treatments below and in Table 1. The data were collected using the Analytical Methods shown herein. The study was conducted using the Feeding and/or Treatment Administration regime shown below.

Study Schedule

| Study Day | Procedure | Measurement | Sample |
|---|---|---|---|
| Pre-Feeding Period | | | |
| Days 0-30 | All dogs receive Control Food | Food Intake daily Body Weight - weekly | |
| Once between Day 23-29 | Tekscan-pressure mapping and DXA-body composition | | |
| Day 30 | Block by age, gender, body fat & assign to groups & foods | | 10 ml blood-Biomarkers & chem. Screen 5 ml Urine-micro-albuminuria & specific gravity |
| Test Feeding Period | | | |
| Days 31-210 | Each group of dogs receive assigned food | Food intake - daily Body weight - weekly | |
| Day 59 | Tekscan-pressure mapping | | 14 ml blood for biomarkers, 5 ml Urine-micro-albuminuria & specfic gravity |
| Day 120 | Tekscan pressure mapping DXA-body composition | | 20 ml blood-Biomarkers & chem. 5 ml Urine-micro-albuminuria & specific gravity |
| Day 210 | Tekscan pressure mapping DXA-body composition | | 20 ml blood-Biomarkers & chem. 5 ml Urine-micro-albuminuria & specific gravity |

TABLE 1

Analyzed Nutrient Profiles of the Four Foods Utilized in the Study

| Nutrients, 100% Dry Matter Basis | Food 61522 | Food 62292 | Food 62794 | Food 62814 |
|---|---|---|---|---|
| Crude Protein, % | 20.10 | 27.65 | 27.76 | 29.39 |
| Fat, % | 16.45 | 13.52 | 11.08 | 13.59 |
| Ca, % | 0.71 | 0.79 | 1.28 | 1.35 |
| P, % | 0.61 | 0.68 | 0.93 | 1.14 |
| EPA, % | 0.32 | 0.10 | <0.01 | 0.10 |
| Linoleic Acid, % | 4.00 | 2.92 | 1.90 | 2.60 |
| Total n-3 fatty acids, % | 1.30 | 0.48 | 0.13 | 0.41 |
| Total n-6 fatty acids, % | 3.96 | 3.10 | 1.79 | 2.66 |
| Taurine, ppm | 1400 | 1090 | <100 | 1600 |
| Carnitine, ppm | 314 | 55 | 19 | 84 |
| Methionine, % | 1.00 | 0.49 | 0.51 | 0.66 |
| Cystine, % | 0.25 | 0.43 | 0.47 | 0.34 |
| Manganese, ppm | 87 | 77 | 71 | 69 |
| Vitamin E, IU/kg | 1492 | 594 | 894 | 421 |
| Vitamin C, ppm | 127 | 288 | 86 | 21 |

Analytical Methods

Tekscan Pressure Mapping procedure: This procedure involved having dogs walk freely or walk while on a leash across a thin mat placed on the floor. The thin mat contained a thin-film tactile pressure/force sensor which produces accurate and reliable pressure and force readings for each step the animal takes. The mat is connected to a computer that captures the data and the software shows real-time 3D and 2D color displays of the force exerted from each foot as it stepped on the mat. The information was used to compare changes in the forces exerted by each step and then correlated to joint health and arthritis.

Urine Samples Microabluminuria were performed on all urine samples collected during the study.

Blood Samples Blood samples collected on days 0, 30 and 90 were analyzed for arthritic markers, antioxidant status markers, fatty acids, amino acids and chemistry screen to ensure the health of all animals on the study.

Feeding and/or Treatment Administration

Food 61526

| Weight (lbs) | kcal/Day | Dry Food Amount per Day (cups) | Dry Food Amount per Day (cups) |
|---|---|---|---|
| 0.5 | 37 | 1/8 | 1/8-1/8 |
| 1 | 62 | 1/8 | 1/8-1/4 |
| 1.5 | 84 | 1/4 | 1/4-1/4 |
| 2 | 104 | 1/3 | 1/4-1/3 |
| 2.5 | 123 | 1/3 | 1/3-3/8 |
| 3 | 141 | 3/8 | 1/3-1/2 |
| 4 | 175 | 1/2 | 3/8-5/8 |
| 5 | 207 | 5/8 | 1/2-2/3 |
| 6 | 237 | 2/3 | 5/8-3/4 |
| 7 | 266 | 3/4 | 5/8-7/8 |
| 8 | 294 | 7/8 | 2/3-1 |
| 9 | 322 | 7/8 | 3/4-1 |
| 10 | 348 | 1 | 7/8-1 1/8 |
| 15 | 472 | 1 1/3 | 1 1/8-1 1/2 |
| 20 | 585 | 1 2/3 | 1 3/8-1 7/8 |
| 25 | 692 | 2 | 1 5/8-2 1/4 |
| 30 | 794 | 2 1/4 | 1 7/8-2 5/8 |
| 40 | 985 | 2 3/4 | 2 1/3-3 1/4 |
| 50 | 1164 | 3 1/4 | 2 3/4-3 7/8 |
| 60 | 1335 | 3 3/4 | 3 1/8-4 3/8 |
| 70 | 1498 | 4 1/4 | 3 1/2-4 7/8 |
| 80 | 1656 | 4 2/3 | 3 7/8-5 3/8 |
| 90 | 1809 | 5 1/8 | 4 1/3-5 7/8 |
| 100 | 1958 | 5 1/2 | 4 5/8-6 3/8 |

Food 62794

| Weight, lbs | Weight, kg | Minimum food, g | Mid point food, g | Maximum, food, g |
|---|---|---|---|---|
| 3-12 | 1.4-5.5 | 53 | 93 | 133 |
| 13-20 | 5.9-9.1 | 133 | 160 | 186 |
| 21-35 | 9.5-15.9 | 186 | 226 | 265 |
| 36-50 | 16.4-22.7 | 265 | 305 | 345 |
| 51-75 | 23.2-34.1 | 345 | 398 | 451 |
| 76-100 | 34.5-45.5 | 451 | 504 | 557 |
| Over 100 | 45.5+ | | | |

Based on standard 8 oz cup (351 kcal/cup, 1510 kcal/lb, 3.3 kcal/gram, 106 gram/cup)

Amounts are recommended for an average adult dog with normal activity. Food intake requirements vary depending on age, activity, and environment, and should be adjusted accordingly.

Food 62814

| Weight, lbs | Weight, kg | Minimum, Grams/day |
|---|---|---|
| 3 | 1.4 | 25 |
| 10 | 4.5 | 80 |
| 20 | 9.1 | 115 |
| 30 | 13.6 | 150 |
| 40 | 18.2 | 185 |
| 50 | 22.7 | 215 |

These guideline amounts are a starting point and your dog may need more food depending upon age, activity and temperament. To reach an optimal body condition, you may need to adjust food intake. Feed this formula to dogs up to 100 lbs, who are 7 years and older.

Food 62292

| Weight, lbs | Weight, kg | Indoor | Activity (1 hr) | Activity (2 hr) |
|---|---|---|---|---|
| 26.4 | 12 | 165 | 185 | 205 |
| 30.8 | 14 | 185 | 205 | 230 |
| 35.2 | 16 | 200 | 230 | 255 |
| 39.6 | 18 | 220 | 250 | 275 |
| 44.0 | 20 | 240 | 270 | 300 |
| 48.4 | 22 | 255 | 285 | 320 |

-continued

| Weight, lbs | Weight, kg | Indoor | Activity (1 hr) | Activity (2 hr) |
|---|---|---|---|---|
| 52.8 | 24 | 270 | 305 | 340 |
| 55.0 | 25 | 280 | 315 | 350 |

Optimal feeding amounts may vary with age, temperament and environment.

Example 2

Feline Study

Study Design: This study utilized 10 healthy geriatric cats (12 years old or over) per group (40 cats total). The cats were determined to be healthy by physical exam and blood chemistry screen. Cats with confirmed renal failure, cancer, arthritis, hyperthyroidism or other diseases were excluded. The cats were located in the Hill's Pet Nutrition Center (Topeka, Kans.) and were cared for in accordance with Institutional Animal Care and Use Committee protocols. The study design utilized a 30 day pre-feeding period followed by a 6 month test feeding period for a total test period of 7 months.

During the 30 day pre-feeding period, all cats were fed the control formula food (Science Diet Senior without the antioxidant package). During the last week of the pre-feeding period, blood samples taken and DXA scans were performed. The cats were then blocked by age, gender and body fat percentage and assigned to 3 different groups. Each group of cats was randomly assigned to receive either the new geriatric food or one of three competitor products. All foods were formulated to meet or exceed AAFCO nutrient recommendations.

During the 7 month test period, blood samples were taken at 1 month, 3 months and 6 months for analysis of biomarkers. Cats were scanned by DXA at 3 months and 6 months to document changes in body composition and bone density. In addition, at 1 month, 3 months and 6 months the cats walked across the Tekscan pressure map to determine effects of the foods on joint health. To assess changes in kidney health, urine microalbuminuria tests were performed at 1 month, 3 months and 6 months. Throughout the duration of the study, body weight was recorded weekly and food intake recorded daily. Additionally, cats were offered enrichment toys, received routine grooming and had daily opportunities for socialization with other cats and people.

Data was taken according to the Study Schedule shown below. The foods used in the study are shown in the Study Treatments below and in Table 2. The data were collected using the Analytical Methods shown herein. The study was conducted using the Feeding and/or Treatment Administration regime shown below.

The results of the study were analyzed to determine the effects of various foods, food components, and nutrients on inflammatory disease and their usefulness for the prevention and/or treatment of inflammatory disease. The results show that compositions comprising omega-3 fatty acids, one or more sulfur containing amino acids, and manganese are beneficial for preventing and/or treating inflammatory disease.

Study Schedule

| Study Day | Procedure | Measurement | Sample |
|---|---|---|---|
| Pre-Feeding Period | | | |
| Days 0-30 | All cats receive Control Food | Food Intake daily Body weight - weekly | |
| Once between Day 23-29 | Tekscan-pressure mapping and DXA-body composition | | |
| Day 30 | Block by age, gender, body fat & assign to groups & foods | | 10 ml blood-Biomarkers & chem. Screen 5 ml Urine-microalbuminuria & specific gravity |
| Test Feeding Period | | | |
| Days 31-210 | Each group of dogs receive assigned food | Food intake - daily Body weight - weekly | |
| Day 59 | Tekscan-pressure mapping | | Collect 15 ml whole blood (Serum) for biomarkers, 5 ml Urine-microalbuminuria & specific gravity |
| Day 120 | Tekscan pressure mapping DXA-body composition | | 15 ml blood-Biomarkers & chem. Screen, 5 ml Urine-microalbuminuria & specific gravity |
| Day 210 | Tekscan pressure mapping DXA-body composition | | 10 ml blood-Biomarkers & chem. screen, 5 ml Urine-microalbuminuria & specific gravity |

TABLE 2

Analyzed Nutrient Profiles of the Four Foods Utilized in the Study

| Key Nutrients, 100% Dry Matter Basis | Food 61526 | Food 62264 | Food 62695 | Food 62779 |
|---|---|---|---|---|
| Crude Protein, % | 35.73 | 34.85 | 30.52 | 40.45 |
| Fat, % | 22.47 | 15.39 | 23.63 | 15.69 |
| Ca, % | 0.94 | 1.22 | 0.80 | 1.38 |
| P, % | 0.77 | 1.05 | 0.72 | 1.30 |
| DHA, % | 0.23 | 0.08 | 0.11 | 0.07 |
| EPA, % | 0.32 | 0.07 | 0.13 | 0.07 |
| Linoleic Acid, % | 5.05 | 2.78 | 4.78 | 2.17 |
| Total n-3 fatty acids, % | 1.14 | 0.28 | 0.74 | 0.32 |
| Total n-6 fatty acids, % | 5.09 | 2.87 | 5.02 | 2.13 |
| Taurine, ppm | 2100 | 1800 | 1600 | 2100 |
| Carnitine, ppm | 367 | 28 | 90 | 28 |
| Methionine, % | 1.32 | 1.05 | 0.72 | 0.77 |
| Cystine, % | 0.47 | 0.38 | 0.51 | 0.53 |
| Manganese, ppm | 104 | 63 | 70 | 73 |
| Vitamin E, IU/kg | 1292 | 390 | 608 | 964 |
| Vitamin C, ppm | 141 | 12 | 511 | 110 |

Analytical Methods

Tekscan Pressure Mapping procedure: This procedure involved having cats walk freely across a thin mat placed on the floor. The thin mat contained a thin-film tactile pressure/force sensor which produces accurate and reliable pressure and force readings for each step the animal takes. The mat is connected to a computer that captures the data and the software shows real-time 3D and 2D color displays of the force exerted from each foot as it stepped on the mat. The information was used to compare changes in the forces exerted by each step and then correlated to joint health and arthritis.

Urine Samples: Microablumeria were performed on all urine samples collected during the study.

Blood Samples: Blood samples collected on days 30, 59 and 120 and 210 were analyzed for arthritic markers, antioxidant status markers, fatty acids, amino acids and chemistry screen to ensure the health of all animals on the study.

Feeding and/or Treatment Administration

Food 61526

| Weight (lbs) | kcal/Day | Dry Food Amount per Day (cups) | Dry Food Amount per Day (cups) |
|---|---|---|---|
| 0.5 | 28 | 1/8 | 1/8-1/8 |
| 1 | 46 | 1/8 | 1/8-1/8 |
| 1.5 | 63 | 1/8 | 1/8-1/8 |
| 2 | 78 | 1/4 | 1/8-1/4 |
| 2.5 | 92 | 1/4 | 1/4-1/4 |
| 3 | 106 | 1/4 | 1/4-1/3 |
| 4 | 131 | 1/3 | 1/4-3/8 |
| 5 | 155 | 3/8 | 1/3-1/2 |
| 6 | 178 | 1/2 | 3/8-1/2 |
| 7 | 200 | 1/2 | 3/8-5/8 |
| 8 | 221 | 1/2 | 1/2-5/8 |
| 9 | 241 | 5/8 | 1/2-2/3 |
| 10 | 261 | 2/3 | 1/2-3/4 |
| 15 | 354 | 7/8 | 3/4-1 |

Food 62779

| Weight, lbs | Weight, kg | Minimum food, g | Mid point food, g | Maximum, food, g |
|---|---|---|---|---|
| 5-9 | 2-4 | 35 | 44 | 53 |
| 10-14 | 4-6 | 71 | 89 | 106 |

Feed "free choice" throughout the day, rather than as just a single feeding only at mealtime. Food intake required to maintain ideal body condition will vary, depending on age, activity, and environment.

Food 62264

| Weight, lbs | Weight, kg | Minimum food, g | Mid point food, g | Maximum, food, g |
|---|---|---|---|---|
| 4 | 2 | 25 | 30 | 35 |
| 8 | 4 | 50 | 60 | 70 |
| 12 | 6 | 75 | 88 | 100 |
| 16 | 8 | 95 | 115 | 135 |
| 22 | 10 | 120 | 145 | 170 |

The chart lists the approximate amount of food your cat will need daily to maintain a healthy body weight (Portions are based on the use of a standard 8 ounce measuring cup). Adjust to maintain ideal body weight.

Food 62695

| Weight, lbs | Weight, kg | Lean | Ideal | Overweight |
|---|---|---|---|---|
| 4-7 | 2-3 | 51 | 51 | 41 |
| 7-11 | 3-5 | 82 | 68 | 51 |
| 11-15 | 5-7 | 102 | 89 | 82 |
| 15-22 | 7-10 | 136 | 115 | 102 |

Standard 8 oz measuring cup = 102 grams. Optimal feeding amounts may vary according to your cat's temperament, activity level, and environment.

Calculations and Statistics

Data from both Examples were analyzed using General Linear Models procedure of SAS to determine treatment means. The experimental unit was dog or cat and day 0 was used as a covariate. The geriatric food was then compared to the three competitor foods. Differences were considered significant when $P<0.05$ and trends were determined when $P<0.10$.

Results

The results of the two studies were analyzed to determine the effects of various foods, food components, and nutrients on inflammatory disease and their usefulness for the prevention and/or treatment of inflammatory disease. The results show that compositions comprising one or more omega-3 fatty acids, one or more sulfur containing amino acids, and manganese and food compositions containing one or more omega-3 fatty acids, one or more sulfur containing amino acids, and manganese are beneficial for preventing and/or treating inflammatory disease.

In the specification, there have been disclosed typical preferred embodiments of the invention and, although specific terms are employed, they are used in a generic and descriptive sense only and not for purposes of limitation, the scope of the invention being set forth in the following claims. Obviously many modifications and variations of the present invention are possible in light of the above teachings. It is therefore to be understood that within the scope of the appended claims the invention may be practiced otherwise than as specifically described.

What is claimed is:

1. A pet food composition comprising one or more omega-3 fatty acids, sulfur containing amino acids comprising methionine, cystine and taurine, and manganese in amounts sufficient for preventing or treating inflammatory disease in a patient, wherein the amount of omega-3 fatty acids is from about 30 mg/kg/day to about 3000 mg/kg/day, the amount of the sulfur containing amino acids is from about 1 mg/kg/day to about 200 mg/kg/day and the amount of manganese is from about 0.005 mg/kg/day to about 10 mg/kg/day and at least one food ingredient selected from the group consisting of fats, carbohydrates, proteins, fibers, and nutrients.

2. The composition of claim 1 wherein the omega-3 fatty acids are selected from the group consisting of ALA, DHA, and EPA.

3. The composition of claim 1 wherein the omega-3 fatty acid is EPA.

4. The composition of claim 1 comprising from about 100 mg/kg/day to about 1500 mg/kg/day omega-3 fatty acids, from about 10 mg/kg/day to about 100 mg/kg/day sulfur containing amino acids, and from about 0.05 mg/kg/day to about 5 mg/kg/day manganese.

5. The composition of claim 1 further comprising one or more anti-inflammatory drugs.

6. The composition of claim 1 containing food ingredients in amounts from about 2 weight % to about 50 weight % fat, greater than 0 weight % to about 75 weight % carbohydrate, greater than 0 weight % to about 95 weight % protein, greater than 0 weight % to about 40 weight % dietary fiber, and from 0% to about 15% of one or more nutrients.

7. The composition of claim 1 further comprising one or more anti-inflammatory drugs.

* * * * *